(12) United States Patent
Alocilja (10) Patent No.: US 10,451,579 B2
(45) Date of Patent: *Oct. 22, 2019

(54) NANOPARTICLE-SERIALIZED OLIGONUCLEOTIDE METHODS, COMPOSITIONS, AND ARTICLES

(71) Applicant: BOARD OF TRUSTEES OF MICHIGAN STATE UNIVERSITY, East Lansing, MI (US)

(72) Inventor: Evangelyn C. Alocilja, East Lansing, MI (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/804,039

(22) Filed: Nov. 6, 2017

(65) Prior Publication Data

US 2018/0120251 A1 May 3, 2018

Related U.S. Application Data

(63) Continuation of application No. 14/174,074, filed on Feb. 6, 2014, now Pat. No. 9,810,659.

(60) Provisional application No. 61/763,142, filed on Feb. 11, 2013, provisional application No. 61/762,618, filed on Feb. 8, 2013.

(51) Int. Cl.
*G01N 27/327* (2006.01)
*C12Q 1/6811* (2018.01)
*B82Y 30/00* (2011.01)

(52) U.S. Cl.
CPC ....... *G01N 27/3278* (2013.01); *C12Q 1/6811* (2013.01); *B82Y 30/00* (2013.01)

(58) Field of Classification Search
CPC .................. G01N 27/3278; C12Q 1/6811
See application file for complete search history.

(56) References Cited

U.S. PATENT DOCUMENTS

| 6,261,809 | B1 | 7/2001 | Bertling et al. |
| 8,053,744 | B2 | 11/2011 | Bortolin |
| 8,069,782 | B2 | 12/2011 | Fragala et al. |

(Continued)

OTHER PUBLICATIONS

Anderson et al., One Step Alkaline Synthesis of Biocompatible Gold Nanoparticles Using Dextrin as Capping Agent, *J. Nanopart. Res.*, 13:2843-51 (2011).

(Continued)

*Primary Examiner* — Narayan K Bhat
(74) *Attorney, Agent, or Firm* — Marshall, Gerstein & Borun LLP (57) ABSTRACT

The disclosure relates to the use of nanoparticles that are coated with unique oligonucleotide (e.g., DNA) sequences of various base lengths ("nano-DNA") that act as barcodes for product authentication, product serialization, brand protection, track-and-trace, intelligent supply chain, and law enforcement. The nano-DNA can be incorporated into inks, dyes, resins, labels, and other markings at all manufacturing levels, including the product (unit) level, to encode company and product-specific information. The nano-DNA can also be embedded in the product itself during the manufacturing process. Furthermore, the nano-DNA can be quickly, simply, and inexpensively monitored and verified using an electrochemical biosensor device in resource-limited field conditions.

26 Claims, 5 Drawing Sheets

Specification includes a Sequence Listing.

(56) References Cited

U.S. PATENT DOCUMENTS

| | | |
|---|---|---|
| 8,287,810 B2 | 10/2012 | Alocilja et al. |
| 9,810,659 B2 | 11/2017 | Alocilja |
| 2006/0121181 A1 | 6/2006 | Sleat et al. |
| 2007/0048761 A1 | 3/2007 | Reep et al. |
| 2007/0072197 A1 | 3/2007 | Rayms-Keller et al. |
| 2008/0299667 A1 | 12/2008 | Kwok et al. |
| 2009/0123939 A1 | 5/2009 | Alocilja et al. |
| 2010/0075858 A1 | 3/2010 | Davis et al. |
| 2010/0285985 A1 | 11/2010 | Liang et al. |
| 2011/0171749 A1 | 7/2011 | Alocilja et al. |
| 2012/0315623 A1 | 12/2012 | Alocilja et al. |
| 2014/0024026 A1 | 1/2014 | Alocilja et al. |

OTHER PUBLICATIONS de la Escosura-Muñez et al., Electrochemical analysis with nanoparticle-based biosystems, Trends Anal. Chem., 27(7):568-84 (2008).

USPTO Press Release 13-08 and related transcript for: USPTO, NSF, and NBC Learn Launch 'Science of Innovation' Series, 4 pages published Feb. 11, 2013.

Wang, Nanoparticle-Based Electrochemical DNA Detection, *Analytica Chimica Acta,* 500:247-57 (2003).

Zhang et al., Fluorescent bio-barcode DNA assay for the detection of *Salmonella enterica* serovar Enteritidis, *Biosensors and Bioelectronics,* 24:1377-81 (2009).

Zhang et al., A Multiplex Nanoparticle-Based Bio-Barcoded DNA Sensor for the Simultaneous Detection of Multiple Pathogens, *Biosensors and Bioelectronics,* 26:1736-42 (2010).

NANOPARTICLE-SERIALIZED OLIGONUCLEOTIDE METHODS, COMPOSITIONS, AND ARTICLES

CROSS REFERENCE TO RELATED APPLICATIONS

Priority is claimed to U.S. Provisional Application Nos. 61/762,618 (filed Feb. 8, 2013) and 61/763,142 (filed Feb. 11, 2013), each of which is incorporated herein by reference in its entirety.

STATEMENT OF GOVERNMENT INTEREST

None.

BACKGROUND OF THE DISCLOSURE

Field of the Disclosure

The disclosure relates to oligonucleotide (e.g., DNA)-based signature technology incorporating nanoparticle label and separation/recovery moieties which can be monitored quickly, simply, and inexpensively under resource-limited field settings.

Brief Description of Related Technology

Product counterfeiting is a serious global challenge for legitimate manufacturers and customers. A flood of sham products undermines the software, computer hardware, pharmaceutical, food, entertainment, and fashion industries—everything from fake designer jeans to phony prescription drugs. It is estimated that counterfeit products account for about 5-7% of world trade, worth an estimated US$600 billion a year. Counterfeiting is a rapidly growing business. It is a serious threat to public safety, equity, revenue, job markets, and taxes around the world. For example, counterfeit medicines usually do not contain the appropriate active ingredient, causing more harm to the patient and allowing microbes to develop drug resistance. Knock-off toys are not up to code against choking hazards or paint toxicity. Thus, the impact of product counterfeiting is long-term, subtle and diffuse.

Because counterfeit electronic parts adversely affect safety, pose significant risks to the U.S. government defense supply chain, and drive up costs, the Pentagon's Defense Logistics Agency (DLA) has enacted a DNA-marking requirement of all items falling within Federal Supply Class 5962 (Electronic Microcircuits) requiring all such electronic microcircuits to include a contractor-unique DNA-based signature.

SUMMARY

The disclosure relates to the use of nanoparticles that are coated with unique oligonucleotide (e.g., DNA) sequences of various base lengths ("nano-DNA") that act as barcodes for product authentication, product serialization, brand protection, track-and-trace, intelligent supply chain, and law enforcement. The nano-DNA can be incorporated into inks, dyes, resins, labels, and other markings at all manufacturing levels, including the product (unit) level, to encode company and product-specific information. The nano-DNA can also be embedded in the product itself during the manufacturing process. Furthermore, the nano-DNA can be quickly, simply, and inexpensively monitored and verified using an electrochemical biosensor device in resource-limited field conditions.

The disclosed DNA-based anti-counterfeiting technology can be uniquely designed for each company and for each product. A nanoparticle coated with a DNA sequence having a base length of N will generate N factorial (N!) unique codes. For example, a DNA sequence of base length 10 will generate 3.6 million unique codes (10!); a DNA base length of 20 will generate up to 20! or $2.4 \times 10^{18}$ (2.4 quintillion) unique codes. The length of a serialized oligonucleotide marker and the corresponding number unique codes can be uniquely selected for any given company, manufacturing facility, product type, product lot, product serial number. Such anti-counterfeiting technology is very difficult to copy as it is uniquely different for each company or product in terms of sequence and base length. Furthermore, the technology can be read simply and inexpensively with an electrochemical biosensor, thus allowing for field-operability, quick results, and inexpensive operation.

By comparison, other DNA-based anti-counterfeiting technologies require expensive PCR machines and highly skilled personnel to operate. Thus, the use of such technologies has been limited to major companies that can afford to maintain DNA-lab facilities or pay for expensive screening.

In contrast, the disclosed anti-counterfeiting approach is inexpensive, quick, and simple, thus allowing for more frequent screening of products at very affordable cost. The technology can be used to protect pharmaceutical products, imported foods, electronics, currency, credit cards, passports, and many other legal documents and goods (e.g., incorporated into the product itself, incorporated into the product packaging, printed onto the product or product packaging).

In one aspect, the disclosure relates to a method of identifying an article of manufacture, the method comprising: (a) providing an article comprising a first serialized oligonucleotide-nanoparticle comprising a first nanoparticle core and at least one first serialized oligonucleotide (e.g., single-stranded oligonucleotide) attached thereto, wherein the first serialized oligonucleotide has an oligonucleotide base sequence corresponding to a unique preselected code defining one or more identifying indicia of the article; (b) providing a second serialized oligonucleotide-nanoparticle comprising a second nanoparticle core and at least one second serialized oligonucleotide (e.g., single-stranded oligonucleotide) attached thereto, wherein the second serialized oligonucleotide has an oligonucleotide base sequence at least partially complementary to the first serialized oligonucleotide and capable of hybridizing thereto; (c) combining (i) at least one of the article and a sample thereof containing the first serialized oligonucleotide-nanoparticle and (ii) the second serialized oligonucleotide-nanoparticle under conditions sufficient for hybridization between the first serialized oligonucleotide and the second serialized oligonucleotide, thereby forming a nanoparticle complex comprising the first nanoparticle core attached to the second nanoparticle core via the hybridized first and second serialized oligonucleotides; (d) separating the nanoparticle complex from the article or the sample components remaining after nanoparticle complex formation, thereby forming a purified nanoparticle complex; and (e) electrochemically detecting the at least one of the first nanoparticle core and the second nanoparticle core in the purified nanoparticle complex, thereby determining at least one of the identifying indicia corresponding to the preselected code of the first serialized oligonucleotide.

In another aspect, the disclosure relates to kit (or system) for identifying an article of manufacture, the method comprising, the kit (or system) comprising: (a) a first serialized oligonucleotide-nanoparticle comprising a first nanoparticle core and at least one first serialized oligonucleotide attached thereto, wherein the first serialized oligonucleotide has an oligonucleotide base sequence corresponding to a unique preselected code defining one or more identifying indicia of an article; (b) a second serialized oligonucleotide-nanoparticle comprising a second nanoparticle core and at least one second serialized oligonucleotide attached thereto, wherein the second serialized oligonucleotide has an oligonucleotide base sequence at least partially complementary to the first serialized oligonucleotide and capable of hybridizing thereto; and (c) optionally a database comprising the first serialized oligonucleotide base sequence, the unique preselected code and identifying indicia associated therewith, the second serialized oligonucleotide base sequence, and the unique preselected code and identifying indicia associated therewith (e.g., electronic database stored in a computer-readable medium; codes/indicia can be the same or different such as one information set is a subset of the other information set).

In another aspect, the disclosure relates to a method for making or testing an identifiable article of manufacture, the method comprising: (a) providing a kit or system for identifying an article of manufacture according to any of the disclosed embodiments; (b) affixing the first serialized oligonucleotide-nanoparticle to an article (e.g., the article as the product itself or the article as a label/packaging for the product); and (c) releasing the article into a commercial stream at a first point. In an extension, the method further comprises (d) recovering the article from the commercial stream at a second point (different from the first point); (e) combining (i) at least one of the article and a sample thereof containing the first serialized oligonucleotide-nanoparticle and (ii) the second serialized oligonucleotide-nanoparticle under conditions sufficient for hybridization between the first serialized oligonucleotide and the second serialized oligonucleotide, thereby forming a nanoparticle complex comprising the first nanoparticle core attached to the second nanoparticle core via the hybridized first and second serialized oligonucleotides; (f) separating the nanoparticle complex from the article or the sample components remaining after nanoparticle complex formation, thereby forming a purified nanoparticle complex; and (g) electrochemically detecting the at least one of the first nanoparticle core and the second nanoparticle core in the purified nanoparticle complex, thereby determining at least one of the identifying indicia corresponding to the preselected code of the first serialized oligonucleotide (e.g., by looking up the preselected code or portion thereof of the first serialized oligonucleotide in the electronic database).

Various refinements and extensions of the disclosed methods, kits, systems, and associated compositions (e.g., serialized oligonucleotide compositions and related complexes) are possible. For example, (i) the first nanoparticle core comprises a metal (e.g., a nanoparticle formed entirely from one or more metals, a nanoparticle core having one or more metal components, where the metal/metal component is suitable for electrochemical detection); and/or (ii) the second nanoparticle core comprises a magnetic material (e.g., suitable for magnetic separation of the nanoparticle complex from a sample medium). Similarly, (i) the first nanoparticle core comprises a magnetic material; and/or (ii) the second nanoparticle core comprises a metal. In any embodiment, the magnetic material can be selected from the group consisting of magnetic iron oxides (e.g., $Fe_2O_3$, $Fe_3O_4$; such as nanoparticles formed from the magnetic material alone or combined with another non-magnetic material, for example a non-magnetic metal, a conductive polymer, or a non-conductive polymer (in a magnetic core-non-magnetic shell configuration or otherwise)). In any embodiment, the metal can be selected from the group consisting of lead, cadmium, zinc, copper, tin, gold, silver, platinum, palladium, ruthenium, rhodium, osmium, iridium, composites thereof, alloys thereof, salts thereof (e.g., sulfates, sulfites, sulfides, chlorides, other halide salts, phosphates, nitrates, nitrites), and combinations thereof. In various refinements, the first nanoparticle core and the second nanoparticle core each independently have a size of at least 1 nm, 2 nm, 5 nm, 10 nm, 20 nm, 50 nm, or 100 nm and/or up to 10 nm, 20 nm, 50 nm, 100 nm, 200 nm, 500 nm, or 1000 nm (e.g., diameter or other characteristic dimension; average size such as weight-, number-, or volume-average of a distribution of nanoparticles; can apply to metal and/or magnetic nanoparticle cores).

In further refinements, the first serialized oligonucleotide and the second serialized oligonucleotide each independently have at least 5, 10, 15, 20, 30, or 40 bases and/or up to 10, 15, 20, 30, 40, 60, or 100 bases forming their respective oligonucleotide base sequences. In an embodiment, the first serialized oligonucleotide and the second serialized oligonucleotide have the same coding lengths (e.g., or overall length; coding length reflects the number of bases corresponding to the preselected code/identifying information is the same for both serialized oligonucleotides, although additional non-coding bases may be present in either or both serialized oligonucleotides for other non-coding/identification purposes, such that coding lengths are the same but overall lengths may be different; such as when they both define the same code/identifying information). In another embodiment, the first serialized oligonucleotide and the second serialized oligonucleotide have different coding lengths (e.g., such as when one sequence defines a code/identifying information that is a subset of the other sequence information).

In another refinement, (i) the article comprises a plurality of first serialized oligonucleotide-nanoparticles; (ii) each first nanoparticle core comprises a metal; and (iii) the plurality of first serialized oligonucleotide-nanoparticles comprises a plurality of different metals in a preselected ratio corresponding to an additional preselected code defining one or more additional identifying indicia of the article (e.g., each nanoparticle core contains a single metal or a combination of metals, where the combination/ratio of metals in the plurality as a whole defines a characteristic spectrum that can be electrochemically detected to determine/differentiate other spectra).

In another refinement, the detection/testing methods further comprises performing at least one of PCR analysis or DNA sequencing analysis on the purified nanoparticle complex to determine all or a portion of the oligonucleotide base sequence of at least one of the first serialized oligonucleotide and the second serialized oligonucleotide (e.g., as a confirmation of the electrochemical detection and/or to provide further identification, such as when the electrochemical detection identifies only a subset of information associated with the first serialized oligonucleotide). In an alternative embodiment, PCR and/or DNA sequencing analysis can be used instead of electrochemical detection of the nanoparticle complex (e.g., only the first serialized oligonucleotide-nanoparticle is recovered/analyzed from the article, and the second serialized oligonucleotide-nanoparticle is not a required component of the method or related compositions, kits, systems, etc.).

In further refinements, the article is selected from the group consisting of electronic/computer hardware, software encoded in a tangible medium, a pharmaceutical composition, a medical device, a legal/financial instrument (e.g., paper or coin currency, credit card or electronically encoded card such as for performing a financial transaction), a food item, and packaging for a product (e.g., the foregoing articles or otherwise as products; container, label, box, paper, cardboard, plastic packaging, etc.). In another refinement, the first serialized oligonucleotide-nanoparticle is incorporated into the article in at least one medium selected from the group consisting of an (invisible or visible) ink applied to the article or a packaging material therefor, a label applied to the article or a packaging material therefor, and a resin or polymer medium as a component of or applied to the article or a packaging material therefor. In another refinement, the identifying indicia are selected from the group consisting of source information, supply chain information, product information, and combinations thereof (e.g., any or all of company/supplier name/address, production facility, shipping facility, product information such as product code, lot, facility, unit identifier (e.g., serial number for an individual unit item), dates associated with any production/shipping events, etc.; both serialized oligonucleotides can encode the same identifying indicia (e.g., as complete complements of each other) or one serialized oligonucleotide can encode a subset of information from the other serialized oligonucleotide).

More generally, the methods herein can be applied to the testing of an article suspected of containing the first serialized oligonucleotide-nanoparticle. In this way, a negative result for the electrochemical detection of the first or second nanoparticle core can be used to identify the article as non-authentic/counterfeit. A positive result can confirm or suggest the article's authenticity (e.g., subject to further testing such as PCR or sequencing). Additionally, a positive result can be used to trace the history of a product, for example where the authenticity of an article is not necessarily in question, but where it is desirable to know the particular article's history in the stream of commerce.

Additional features of the disclosure may become apparent to those skilled in the art from a review of the following detailed description, taken in conjunction with the drawings, examples, and appended claims.

BRIEF DESCRIPTION OF THE DRAWINGS

For a more complete understanding of the disclosure, reference should be made to the following detailed description and accompanying drawings wherein.

While the disclosed compositions, articles, and methods are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

Figure 1:
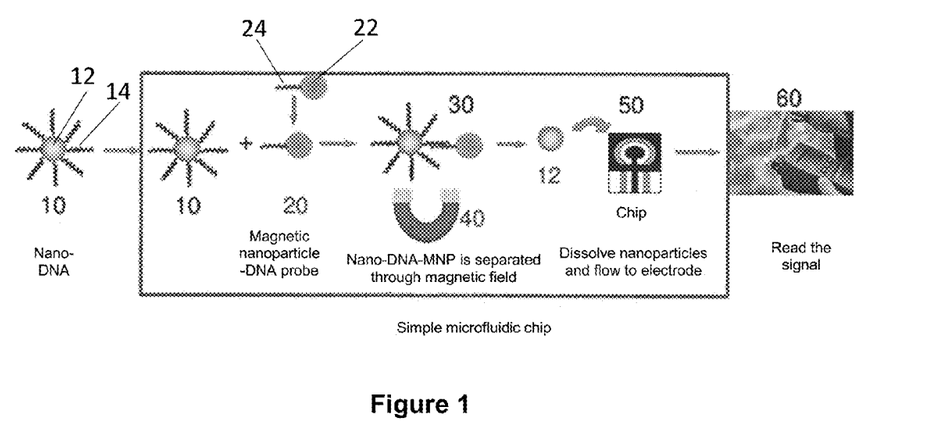
FIG. 1 illustrates a schematic of a nano-DNA detection process according to the disclosure.
Figure 1A:
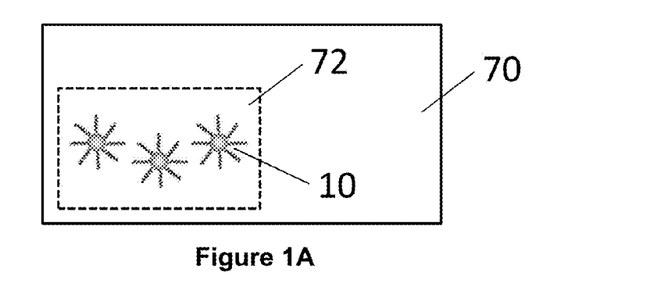
FIG. 1A illustrates a product or article including a serialized oligonucleotide-nanoparticle label/tracer according to the disclosure.
Figure 1B:
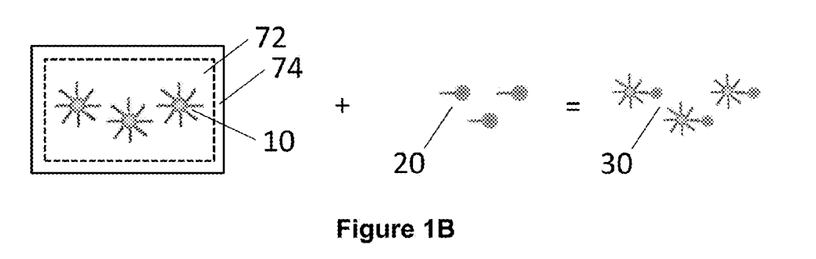
FIG. 1B illustrates a sampling process for a labeled product or article to form a detectable nanoparticle complex according to the disclosure.

The principle behind the nano-DNA technology is presented in FIG. 1. The nano-DNA 10 (e.g., gold nanoparticles 12 conjugated with serialized oligonucleotides 14) could be incorporated in product (or article) 70 markings, packages, or embedded in the product 70 itself at a specific location 72 (FIGS. 1 and 1A). During authentication, a sample 74 of the product 70 containing the nano-DNA 10 is removed and hybridized with a complementary nano-DNA 20 (e.g., magnetic nanoparticles 22 conjugated to serialized oligonucleotides 24, at least a portion of which are complementary to those of the serialized oligonucleotides 14 of the nano-DNA 10) to form a two-component nano-DNA conjugate/complex 30 (FIGS. 1 and 1B). For example, the nano-DNA 10 (e.g., from the product 70 or sample 74 thereof) and the nano-DNA 20 can be added to an aqueous medium (e.g., a physiological buffer) under time and temperature conditions suitable for hybridization of the serialized oligonucleotides 14, 24 to form the complex 30. The complex 30 can be separated from the aqueous medium (e.g., magnetically separated from other product 70/sample 74 components with a magnet 40 when at least one of the nanoparticles 12, 22 is magnetic/magnetically attractable), washed, and then prepared for further analysis (e.g., prepared as a concentrated suspension). The specific method for detecting the nano-DNA conjugate/complex 30 (e.g., detecting the either or both of the nanoparticle cores 12, 22 thereof, electrochemically or otherwise) is not particularly limited. In an illustrative electrochemical detection method, the nano-DNA complex 30 is then added to a microfluidic chip 50 that is connected to an electrochemical reader 60. The microfluidic chip 50 will process the sample internally and the final solution is flowed into an electrode chip (e.g., including acidic dissolution of the complex 30 to form metal ions corresponding to the metal nanoparticles 12, 22 of the nano-DNA 10 and/or 20 (e.g., a metallic component of the first and/or second nanoparticle cores 12, 22 thereof); application of same to a working surface/electrode of a chip 50 such as an SPCE). Upon application of a voltage to the chip 50, the electrochemical reaction occurs and a signal, in the form of an electric current, is generated. This electrical signal reports the presence of the nano-DNA 10 and/or 20 signature (e.g., confirming the product's authenticity when present).

The gold nanoparticles 12 can be replaced with any metallic nanoparticles and their related forms, such as silver (Ag), lead (Pb), lead sulfide (PbS), cadmium (Cd), cadmium sulfide (CdS), zinc (Zn), zinc sulfide (ZnS), etc. The magnetic nanoparticles 22 can be replaced with $Fe_2O_3$, $Fe_3O_4$, magnetic-polyaniline, magnetic-polypyrrole, magnetic-silica, etc. The electrochemical reader 60 can be in any form and size such as handheld, benchtop, etc.

EXAMPLE

The following example illustrates the disclosed processes and compositions, but is not intended to limit the scope of any claims thereto.

Figure 2:
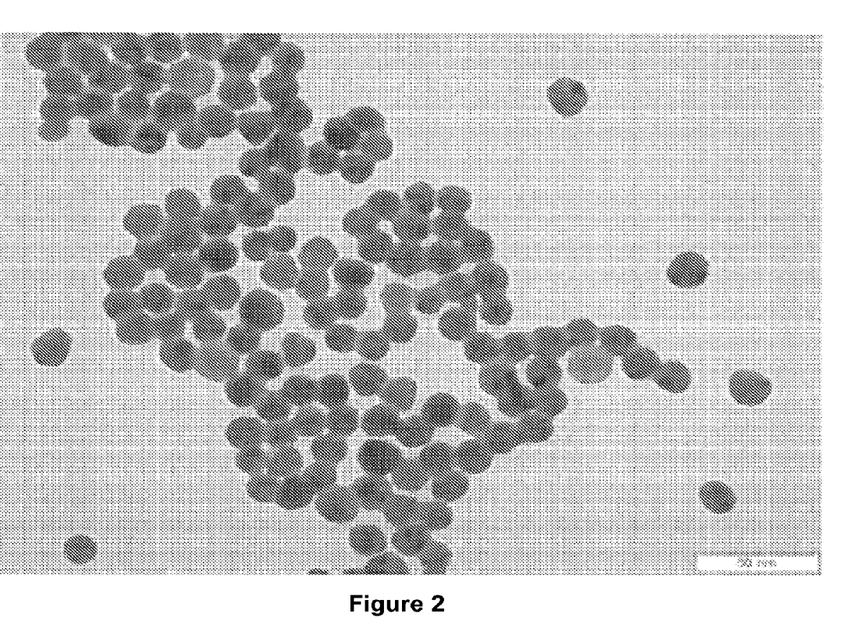
FIG. 2 is a TEM image of dextrin gold nanoparticles having an average diameter of about 15 nm.
Figure 3:
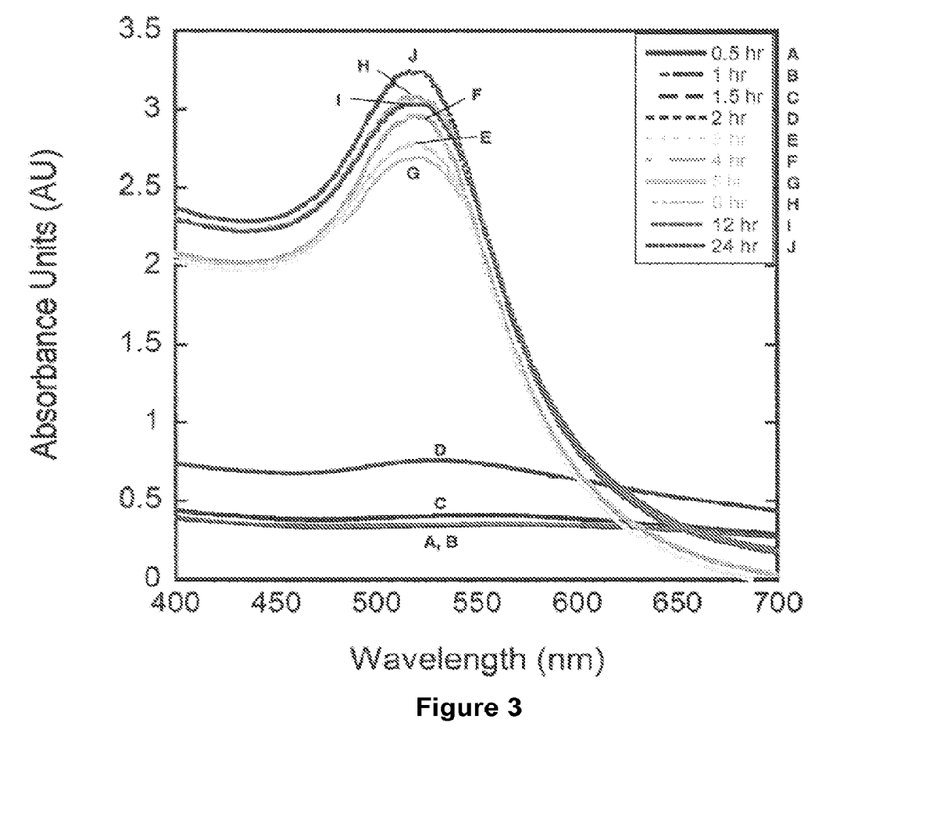
FIG. 3 is a graph illustrating the UV-vis absorption of dextrin gold nanoparticles at 520 nm wavelength.

Gold nanoparticles (AuNPs) were synthesized under alkaline condition following the approach published by Anderson et al (2011). Briefly, 20 ml of dextrin stock solution (25 g/l) and 20 ml of sterile water were mixed in a 50 ml sterile orange cap tube (disposable). Five milliliters of $HAuCl_4$ stock solution (8 g/ml) were then added, and the pH of the solution was adjusted to 9 with sterile 10% (w/v) $Na_2CO_3$ solution. The final volume was brought to 50 ml with pH 9 water. The reaction was carried out by incubating the solution in a sterile flask in the dark at 50° C. with continuous shaking (100 rpm) for 6 h. A red solution was obtained at the end of the reaction. The final concentration of AuNP was 10 mg/ml. FIG. 2 shows a transmission electron microscope (TEM) image of gold nanoparticles with about 15 nm in diameter. They have been characterized for UV-vis absorption at 520 nm (FIG. 3) and for their electrochemical properties.

The AuNPs were coated with synthetic oligonucleotides (sequence length may vary, preferably from 5 to 30 bases). Briefly, thiolated oligonucleotides were mixed with 100 μl of 0.1 M DTT solution and then purified using a Nap-5 column. The oligonucleotides (5 nmol) were added to 1 ml of AuNPs and a serial salt addition was conducted for 3 h. The thiolated DNA would form a self-assembled monolayer on the surface of AuNPs. After washing away the excess reagents, the AuNP-DNA conjugates (or nano-DNA) were ready for use and could be stored at room temperature.

Figure 4:
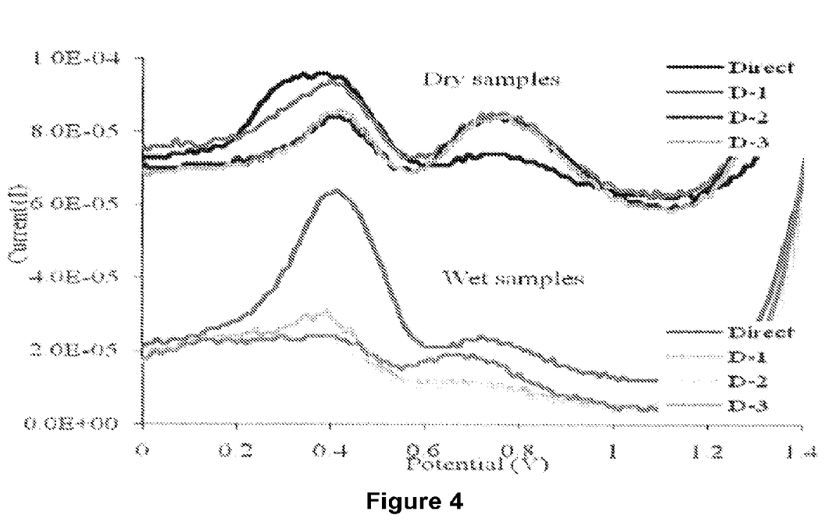
FIG. 4 is a graph illustrating the differential pulse voltammetric detection of different concentrations of nano-DNA under wet or dry conditions.

The foregoing procedure was used to attach two validation oligonucleotide sequences to the AuNPs: 5'-AATAT-GCTGCCTACTGCCCTACGCTT-SH-3' (SEQ ID NO:1; 26 bases) and 5'-AGATTTAAATCTGGTAGAAAGGCGG-SH-3' (SEQ IS NO: 2; 25 bases). Both sequences could be detected using AuNPs as electrochemical reporters as shown in FIG. 4 (differential pulse voltammogram of different nano-DNA concentrations on screen carbon printed electrodes (SPCE); D-1=1:10 dilution, D-2=1:100 dilution, D-3=1:1000 dilution). Wet samples were detected immediately with minimum or no accumulation time. The AuNP dissolution with HCl was performed in liquid before the sample was transferred to the SPCE. Dry samples were deposited on the SPCE and the HCl was applied after the solution was completely dry.

Conjugation of magnetic nanoparticles (MNPs) with DNA probes (having matching/complementary sequences to the oligonucleotides conjugated to the AuNPs) could be performed in various ways depending on the type of magnetic nanoparticles used. One way is to use polyamine-functionalized iron oxide (PIO) particles. In this method (Zhang et al., 2009; Zhang et al., 2010), 1 mg of PIO were reacted with 300 μg of sulfo-SMCC bifunctional linker for 2 h in 1 mL coupling buffer (0.1 M PBS buffer, 0.2M NaCl, pH 7.2). After rinsing, the reduced thiolated DNA probe (1 nmol) was added into 1 mL coupling buffer containing sulfo-SMCC-modified MNPs and reacted for 8 h. The functionalized MNPs were then suspended in 35 mL of 10 mM sulfo-NHS acetate. The solution was incubated and shaken at room temperature to block the unreacted sulfo-SMCC on the surface of MNPs. After passivation, the particles were centrifuged at 4000 rpm for 1 min and washed with passivation buffer (0.2M Tris, pH 8.5) and then with a storage buffer (10 mM PBS buffer, 0.2M NaCl, pH 7.4). The MNP-probe conjugates were stored at 4° C. before use.

Figure 5A:
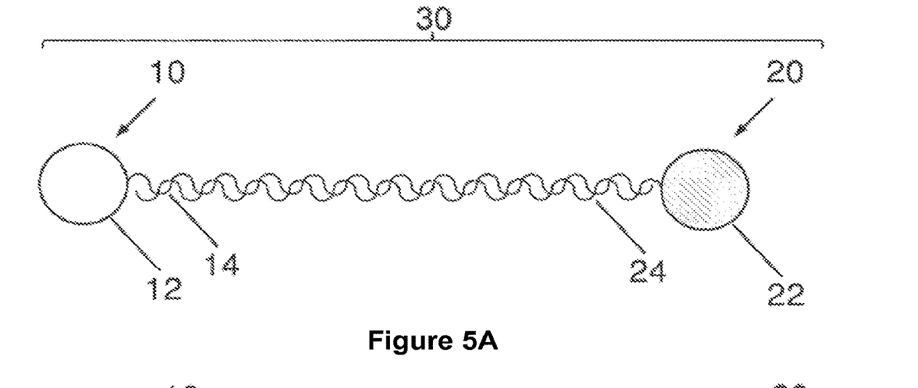
FIGS. 5A-5C illustrate various embodiments of first and second serialized oligonucleotide-nanoparticles and related complexes according to the disclosure.

FIGS. 5A-5C illustrate various embodiments of first and second serialized oligonucleotide-nanoparticles and related complexes according to the disclosure. In FIG. 5A, a nanoparticle complex 30 includes a first serialized oligonucleotide-nanoparticle 10 and a second serialized oligonucleotide-nanoparticle 20. The first serialized oligonucleotide-nanoparticle 10 includes a first nanoparticle core 12 and a first serialized oligonucleotide 14 attached thereto (illustrated as a single oligonucleotide 14, although the core 12 can have a plurality of attached oligonucleotides 14). Similarly, the second serialized oligonucleotide-nanoparticle 20 includes a second nanoparticle core 22 and a second serialized oligonucleotide 24 attached thereto (illustrated as a single oligonucleotide 24, although the core 22 can have a plurality of attached oligonucleotides 24). The first and second serialized oligonucleotides 14, 24 are hybridized together, linking the nanoparticle cores 12, 22 and forming the complex 30 (e.g., as originally formed in a sample analysis or sample matrix, or as subsequently purified from a sample matrix for electrochemical detection).

Figure 5B:
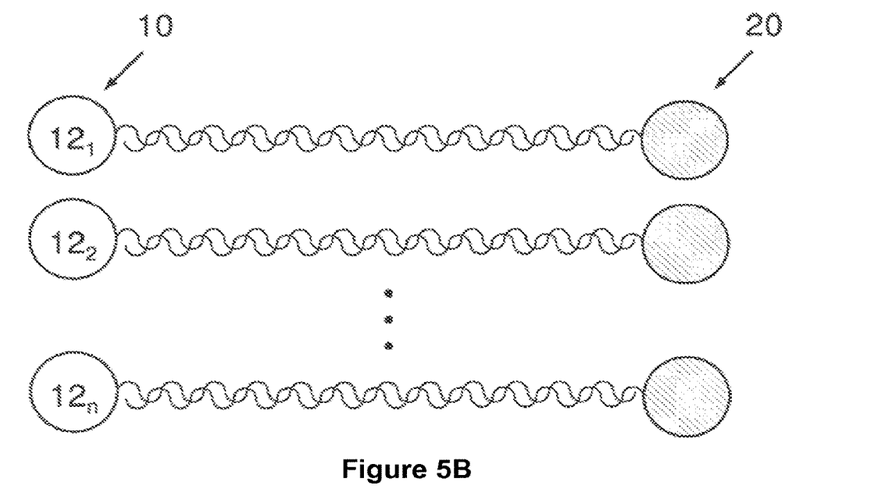

FIG. 5B illustrates an embodiment in which the first serialized oligonucleotide-nanoparticle composition 10 incorporated into an article 70 includes a plurality of first serialized oligonucleotide-nanoparticles 10 containing a plurality of different metal nanoparticle cores 12, (e.g., for i=1 to n different metals/metal combinations). The different metal nanoparticle cores 12, are incorporated into an article 70 in a preselected ratio corresponding to an additional preselected code defining one or more additional identifying indicia of the article. As an illustration, a given set of 3 different metal nanoparticle cores $12_1$, $12_2$, and $12_3$ having the same first serialized oligonucleotide 14 may be incorporated into different articles at ratios of 1:1:1 and 1:2:1 (for example). By electrochemically resolving the differing ratios, the predetermined plurality of different metal nanoparticle cores 12, and corresponding ratios can be used to extend the coding information contained in the first serialized oligonucleotide 14.

Figure 5C:
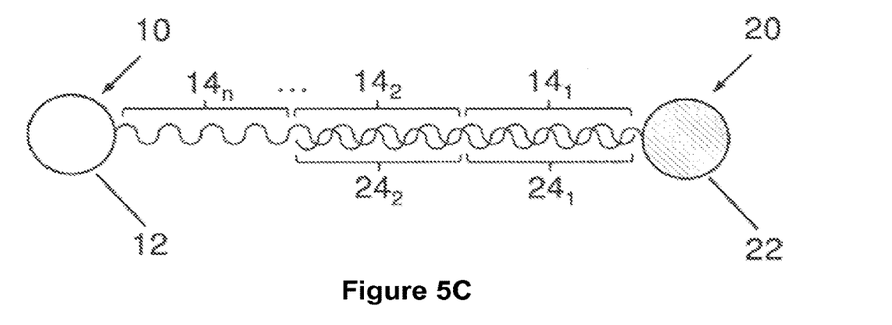

FIG. 5C illustrates an embodiment in which the first serialized oligonucleotide 14 and the second serialized oligonucleotide 24 have different coding lengths (e.g., such as when one sequence defines a code/identifying information that is a subset of the other sequence information). For example, the first serialized oligonucleotide 14 can be represented by a series of coding regions 14, (e.g., for i=1 to n), where each region 14, corresponds to a particular subset of all of the code/information denoted by the oligonucleotide 14. Similarly, the second serialized oligonucleotide 24 can be represented by a series of coding regions 24, (e.g., for i=1 to m, where m<n), where each region 24, corresponds to a particular subset of all of the code/information denoted by the oligonucleotide 24. For example, as illustrated, regions $14_1$ and $14_2$ could represent the article supplier and product code, respectively, while $14_3$ to $14_n$ could represent more detailed product information (e.g., lot number, unit-level serial number). Similarly, complementary regions $24_1$ and $24_2$ also represent the article supplier and product code. In this way, a "universal" second serialized oligonucleotide-nanoparticle 20 composition can be used to rapidly identify top-level information related to a product (e.g., corresponding to coding regions 1 and/or 2 as illustrated), while lower-level information can be subsequently determined using PCR and/or sequencing analysis. As illustrated in FIG. 5C, suitably, when one serialized oligonucleotide is selected to be complementary to a subsequence of the corresponding oligonucleotide, the region for hybridization in the longer base sequence can be selected to be at a terminal region opposite the attachment point of the oligonucleotide to the nanoparticle core.

Nanoparticles

The type and size of the nanoparticles are not particularly limited. The nanoparticles can metal nanoparticles, metal-containing nanoparticles, polymer nanoparticles, polymer-containing nanoparticles, magnetic nanoparticles, and combinations thereof (e.g., as nanocomposites, core-shell nanoparticles, etc.). In various embodiments, the metal or metal-containing nanoparticles can include lead, cadmium, zinc, copper, tin, gold, silver, platinum, palladium, ruthenium, rhodium, osmium, iridium, composites thereof, alloys thereof, salts thereof (e.g., sulfates, sulfites, sulfides, chlorides, other halide salts, phosphates, nitrates, nitrites), and combinations thereof. Suitable metal nanoparticles include gold nanoparticles. Suitable metal-containing nanoparticles include quantum dots (e.g., CdSe, ZnS, CdS, PbS or another metal-containing nanoparticle which can provide an electrochemical detection signal based on its metal component and/or a fluorescent detection signal based on its quantum dot nanocrystal structure). The magnetic nanoparticles can include magnetic iron oxides (e.g., $Fe_2O_3$, $Fe_3O_4$), for example nanoparticles formed from the magnetic material alone or combined with another non-magnetic material (e.g., a non-magnetic metal, conductive polymer, or non-conductive polymer such as in a magnetic core-non-magnetic shell configuration or otherwise). In various embodiments, the first nanoparticle and the second nanoparticle in any of the various forms each independently have a size of at least 1 nm, 2 nm, 5 nm, 10 nm, 20 nm, 50 nm, or 100 nm and/or up to 10 nm, 20 nm, 50 nm, 100 nm, 200 nm, 500 nm, or 1000 nm (i.e., the first and second nanoparticle sizes can be the same or different). Nanoparticle size can represent nanoparticle diameter or other characteristic dimension, for example an average size such as weight-, number-, or volume-average of a distribution of nanoparticles, whether for metal nanoparticles, metal-containing nanoparticles, polymer nanoparticles, polymer-containing nanoparticles, magnetic nanoparticles, or otherwise.

Metal nanoparticles may be formed by any method known in the art. By way of illustration, a suitable method of metal nanoparticle formation includes reduction of metal ions in an aqueous reaction system further including a carbohydrate (or other) capping agent. The metal ions in the aqueous medium are reduced at a neutral or alkaline pH value in the presence of the carbohydrate capping agent under suitable reaction conditions to form reduced metal nanoparticles (e.g., at a reaction temperature and reaction time sufficient to convert all or substantially all of the metal ion precursors). The reaction generally includes an initial nucleation stage to form metallic nuclei followed by a longer growth stage in which metal ions reduced on the nuclei surfaces create the final metal nanoparticles. The reduced metal nanoparticles are in the form of a stabilized suspension of metal nanoparticles in the aqueous medium, where the carbohydrate capping agent stabilizes the formed nanoparticle suspension.

The specific metal ions or oxidized metal-containing species in solution and selected as precursors to the desired metal nanoparticles are not particularly limited and are suitably chosen according to a desired end use/application of the nanoparticle suspension. In an embodiment, the metal ions include gold ions (e.g., Au(III), $Au^{3+}$) and are selected to form gold metal nanoparticles (AuNPs). The metal ions can be free in solution (e.g., introduced into the aqueous medium as a dissolvable ionic compound, for example a salt or acid) or coordinated/coupled with other (ionic) species. Other potential metal ions can include chromium, copper, zinc, nickel, cadmium, silver, cobalt, indium, germanium, tin, lead, arsenic, antimony, bismuth, chromium, molybdenum, manganese, iron, ruthenium, rhodium, palladium, osmium, iridium, and platinum. In some embodiments, two or more types of metal ions can be in solution in the aqueous medium to provide metal nanoparticles formed from alloys of two or more elemental metals. The concentration of metal ions in solution prior to reaction is not particularly limited, but it suitably ranges from 0.1 mM to 1000 mM (e.g., at least 0.1 mM, 1 mM, or 10 mM and/or up to 100 mM or 1000 mM). The population of the reduced metal nanoparticles as produced (e.g., in suspension as formed in the aqueous medium or otherwise) generally has a particle size ranging from 2 nm to 50 nm (e.g., a number-, weight-, or volume-average particle size). For example, the average size of the metal nanoparticle distribution can be at least 2, 5, 8, 10, 12, or nm and/or up to 8, 10, 12, 15, 20, 25, 30, 40, or 50 nm.

In some embodiments, the aqueous medium further includes, prior to reduction of the metal ions, a population of nanoparticles serving as cores/nucleation sites for deposition of the reduced metal ions, thus permitting the formation of metal nanoparticles having a core-shell structure including a nanoparticle core with a metallic shell. The nanoparticle core material is not particularly limited and can be non-metallic, metallic (e.g., different from the metal to be reduced as a shell), magnetic, etc. Magnetic nanoparticle cores are particularly useful to permit the resulting metal nanoparticle to function as both a magnetic sample/analyte separator and concentrator (e.g., due to the magnetic core) as well as a signal transducer (e.g., due to the electrical properties of the metal shell material such as gold).

The magnetic nanoparticles are not particularly limited and generally include any nano-sized particles (e.g., about 1 nm to about 1000 nm) that can be magnetized with an external magnetic/electrical field. For example, the magnetic nanoparticles can include superparamagnetic particles, which particles can be easily magnetized with an external magnetic field (e.g., to facilitate separation or concentration of the particles from the bulk of a sample medium) and then redispersed immediately once the magnet is removed (e.g., in a new (concentrated) sample medium). Thus, the magnetic nanoparticles are generally separable from solution with a conventional magnet. Suitable magnetic nanoparticles are provided as magnetic fluids or ferrofluids, and mainly include nano-sized iron oxide particles ($Fe_3O_4$ (magnetite) or $\gamma$-$Fe_2O_3$ (maghemite)) suspended in a carrier liquid. Such magnetic nanoparticles can be prepared by superparamagnetic iron oxide by precipitation of ferric and ferrous salts in the presence of sodium hydroxide and subsequent washing with water. A suitable source of $\gamma$-$Fe_2O_3$ is Sigma-Aldrich (St. Louis, Mo.), which is available as a nano-powder having particles sized at <50 nm with a specific surface area ranging from about 50 $m^2$/g to about 250 $m^2$/g. Preferably, the magnetic nanoparticles have a small size distribution (e.g., ranging from about 5 nm to about 25 nm) and uniform surface properties (e.g., about 50 $m^2$/g to about 245 $m^2$/g).

More generally, the magnetic nanoparticles can include ferromagnetic nanoparticles (i.e., iron-containing particles providing electrical conduction or resistance). Suitable ferromagnetic nanoparticles include iron-containing magnetic metal oxides, for example those including iron either as Fe(II), Fe(III), or a mixture of Fe(II)/Fe(III). Non-limiting examples of such oxides include FeO, $\gamma$-$Fe_2O_3$ (maghemite), and $Fe_3O_4$ (magnetite). The magnetic nanoparticles can also be a mixed metal oxide of the type $M1_xM2_{3-x}O_4$, wherein M1 represents a divalent metal ion and M2 represents a trivalent metal ion. For example, the magnetic nanoparticles may be magnetic ferrites of the formula $M1Fe_2O_4$, wherein M1 represents a divalent ion selected from Mn, Co, Ni, Cu, Zn, or Ba, pure or in admixture with each other or in admixture with ferrous ions. Other metal oxides include aluminum oxide, chromium oxide, copper oxide, manganese oxide, lead oxide, tin oxide, titanium oxide, zinc oxide and zirconium oxide, and suitable metals include Fe, Cr, Ni or magnetic alloys.

In some embodiments, the nanoparticles can include a conductive polymer (e.g., as the complete nanoparticle; as a coating or shell for a metal and/or magnetic core in a composite nanoparticle). The conductive polymers according to the disclosure are not particularly limited and generally include any polymer that is electrically conductive. Preferably, the conductive polymer is fluid-mobile when bound to an analyte. Suitable examples of conductive polymers are polyanilines, polypyrrole, and polythiophenes, which are dispersible in water and are conductive because of the presence of an anion or cation in the polymer (e.g., resulting from acid-doping of the polymer or monomer). Other electrically conductive polymers include substituted and unsubstituted polyanilines, polyparaphenylenes, polyparaphenylene vinylenes, polythiophenes, polypyrroles, polyfurans, polyselenophenes, polyisothianapthenes, polyphenylene sulfides, polyacetylenes, polypyridyl vinylenes, biomaterials, biopolymers, conductive carbohydrates, conductive polysaccharides, combinations thereof and blends thereof with other polymers, copolymers of the monomers thereof. Conductive polyanilines are preferred. Polyaniline is perhaps the most studied conducting polymer in a family that includes polypyrrole, polyacetylene, and polythiophene. As both electrical conductor and organic compound, polyaniline possesses flexibility, robustness, highly controllable chemical and electrical properties, simple synthesis, low cost, efficient electronic charge transfer, and environmental stability. Addition of a protic solvent such as hydrochloric acid yields a conducting form of polyaniline, with an increase in conductivity of up to ten orders of magnitude. Illustrative are the conductive polymers described in U.S. Pat. Nos. 6,333,425, 6,333,145, 6,331,356 and 6,315,926. Preferably, the conductive polymers do not contain metals in their metallic form.

The conductive polymer provides a substrate for the subsequent attachment of a serialized oligonucleotide bound thereto. The electrically conductive characteristics of the conductive polymer also can facilitate electrochemical detection of a nanoparticle complex including a serialized oligonucleotide-conductive polymer nanoparticle (or conductive polymer-containing nanoparticle), for example by measuring the electrical resistance or conductance through a plurality of conductive polymer nanoparticles immobilized in a capture or detection region of a conductimetric biosensor device.

Serialized Oligonucleotides

Identification and authentication of an article of manufacture according to the disclosure are based on first and second serialized oligonucleotide strands (e.g., single-stranded oligonucleotides or ssDNA strands) that are designed to at least partially (or completely) hybridize. As known to a person skilled in the art, an ssDNA strand contains a 5'-to-3' directionality. Two ssDNA strands will bind (or hybridize) according to the Watson-Crick base paring principle (i.e., an adenine (A) binds to a thymine (T) and a cytosine binds to a guanine (G)). An ssDNA strand or oligonucleotide includes a single free strand of polymerized deoxyribonucleic acids consisting of repeated polymer bases of adenine (A), cytosine (C), guanine (G), and/or thymine (T), where each strand has directionality and runs from five prime (5') to three prime (3'). The two strands when bound together have opposite directionality (i.e., they run anti-parallel). This A/T and C/G base paring is highly specific, and the mismatching rates of such base pairing are very low for relatively short ssDNA sequences. This principle, coupled with preselected sequences for the first and second serialized oligonucleotides which correspond to a unique preselected code/identifying index of an associated article, permits article labeling, identification, and/or authentication.

The length and specific sequences for the first serialized oligonucleotide and the second serialized oligonucleotide are not particularly limited. Relatively longer sequences permit relatively more encoded information to be represented by the serialized oligonucleotides. As used herein, the encoded information includes the preselected codes defining the identifying indicia corresponding thereto (e.g., as contrasted to DNA/oligonucleotide sequences in biological systems which encode amino acid sequences or contain other genetic information in an organism). Relatively longer sequences also reduce the likelihood that either of the serialized oligonucleotides will hybridize with one or more natural DNA/oligonucleotide sequences which may be present in a particular sample being tested (e.g., as a result of a particular product including serialized oligonucleotide-nanoparticles being exposed to the external environment such as in the normal stream of commerce). Suitably, the sequences of the serialized oligonucleotides are selected to be non-complementary to naturally occurring DNA sequences (e.g., unable to hybridize with naturally occurring DNA sequences or known genomic DNA sequences, as in a silent DNA sequence or oligonucleotide) in addition to encoding identifying information. Each serialized oligonucleotide independently can be selected to have at least 5, 10, 15, 20, 30, or 40 bases and/or up to 10, 15, 20, 30, 40, 60, or 100 bases forming its respective oligonucleotide base sequences. In an embodiment, the first serialized oligonucleotide and the second serialized oligonucleotide have the same coding lengths (e.g., or overall length). The coding length reflects the number of bases corresponding to the preselected code/identifying information and can be the same for both serialized oligonucleotides, although additional non-coding bases may be present in either or both serialized oligonucleotides for other non-coding/identification purposes, such that coding lengths are the same but overall lengths may be different (e.g., when both serialized oligonucleotides define the same code/identifying information). In another embodiment, the first serialized oligonucleotide and the second serialized oligonucleotide have different coding lengths (e.g., such as when one sequence defines a code/identifying information that is a subset of the other sequence information).

The first and second serialized oligonucleotides can be produced using methods generally known to those skilled in the art. Suitably, the oligonucleotide sequences may be selected to have from 5 bases to 100 bases (e.g., or from 5 to 30 bases). The first and second serialized oligonucleotides having the desired, preselected sequences generally can be custom ordered from commercial sources (e.g., available from Integrated DNA Technologies; Coralville, Iowa), and such oligonucleotides can be selected to include further functional modifications (e.g., 5'-end and/or 3'-end modification to facilitate serialized oligonucleotide-nanoparticle attachment and/or (hybridized) serialized oligonucleotide-nanoparticle detection, such as with a thiol functional group or fluorescent dye appended to the serialized nucleotide).

The first and second serialized oligonucleotides can be attached to their respective nanoparticle cores to form the corresponding serialized oligonucleotide-nanoparticle structure according to various methods known in the art for a desired nanoparticle application. General methods of oligonucleotide attachment can include physical adsorption (e.g., resulting from electrostatic (metal) nanoparticle-oligonucleotide interactions), direct binding (e.g., based on affinity interactions between the (metal) nanoparticle surface and a functional group of the oligonucleotide, such as between a thiolated oligonucleotide and gold), covalent attachment (e.g., between the oligonucleotide and a covalent linking intermediate that is bound to the (metal) nanoparticle, such as through thiolated carboxylic acids, EDAC-mediated or SMCC-mediated attachment of oligonucleotides, biotin-streptavidin linking, and azide-linking or other "click" functionalization techniques). For example, when attaching serialized oligonucleotides to a conductive polymer-containing nanoparticle (e.g., a magnetic nanoparticle, such as a polyaniline-coated magnetic nanoparticle), oligonucleotides can be incubated in a buffer (e.g., an acetate buffer at a pH of about 5.2) suspension of the nanoparticle that also includes an immunoconjugating agent (e.g., 1-ethyl-3-(3-dimethyl-aminopropyl) carbodiimide hydrochloride ("EDAC")). Similarly, sulfosuccinimidyl-4-(N-maleimidomethyl)cyclohexane-1-carboxylate ("sulfo-SMCC") is a water-soluble, amine-to-sulfhydryl crosslinker suitable for providing a covalent linkage between an amine group (e.g., in a polyamine-functionalized nanoparticle) and a thiol group (e.g., in a thiolated oligonucleotide). In an embodiment, the serialized oligonucleotide can be immobilized on a metal nanoparticle using a ligand exchange process known in the art (e.g., when the metal nanoparticle is stabilized with a capping agent). For example, in a general ligand exchange process, a carbohydrate capping agent stabilizing the metal nanoparticle suspension is removed from the outer surface of the metal nanoparticles (e.g., partial or complete removal of the capping agent). Removal of the capping agent promotes increased access to surface areas of the metal nanoparticles, thus allowing immobilization of the serialized oligonucleotide on the outer surface of the metal nanoparticle (e.g., by contacting/incubating the metal nanoparticle suspension with the serialized oligonucleotide). For example, a suitable ligand exchange method for gold nanoparticles includes a DTT-mediated removal of a (carbohydrate) capping agent followed by immobilization of a thiolated serialized oligonucleotide on the gold nanoparticle surface. Another suitable ligand exchange method for gold nanoparticles includes a surfactant-mediated removal of a (carbohydrate) capping agent followed by immobilization of a thiolated attachment intermediate (e.g., thiolated carboxylic acid used for further covalent attachment of a serialized oligonucleotide) on the gold nanoparticle surface.

The hybridization conditions for forming the nanoparticle complex (e.g., hybridized conjugate between the first and second serialized oligonucleotide-nanoparticles) are not particularly limited and are generally known to the skilled artisan. Suitably, an aqueous mixture or suspension containing the first serialized oligonucleotide-nanoparticles 10 and the second serialized oligonucleotide-nanoparticles 20 (e.g., in a physiological buffer, such as Tris-Saline EDTA at pH 7.4) is heated to a temperature sufficient to initiate hybridization (e.g., at least 25° C., 50° C., or 75° C. and/or up to 95° C.; holding at the maximum heating temperature for 1 min to 5 min) and then allowed to cool (e.g., to room temperature, such as 20° C. to 25° C.), during which time further hybridization occurs.

The various references cited herein and listed below are incorporated by reference in their entireties, in particular in relation to their disclosures related to the formation of nanoparticles and nanoparticle-oligonucleotide conjugates (e.g., magnetic nanoparticles, conductive polymer-coated nanoparticles, gold nanoparticles, and/or other metal nanoparticle tracers alone or conjugated with an oligonucleotide) as well as the detection of same (e.g., magnetic separation/concentration, electrochemical detection).

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

All patents, patent applications, government publications, government regulations, and literature references cited in this specification are hereby incorporated herein by reference in their entirety. In case of conflict, the present description, including definitions, will control.

Throughout the specification, where the compositions, processes, kits, or apparatus are described as including components, steps, or materials, it is contemplated that the compositions, processes, or apparatus can also comprise, consist essentially of, or consist of, any combination of the recited components or materials, unless described otherwise. Component concentrations can be expressed in terms of weight concentrations, unless specifically indicated otherwise. Combinations of components are contemplated to include homogeneous and/or heterogeneous mixtures, as would be understood by a person of ordinary skill in the art in view of the foregoing disclosure.

REFERENCES

1. Alocilja et al. U.S. Pat. No. 8,287,810.
2. Alocilja et al. U.S. Publication No. 2009/0123939.
3. Alocilja et al. U.S. Publication No. 2011/0171749.
4. Alocilja et al. U.S. Publication No. 2012/0315623.
5. Alocilja et al. U.S. Publication No. 2014/0024026.
6. Anderson, J. M., Torres-Chavolla, E., Castro, A. B., and Alocilja, E. C. 2011. One step alkaline synthesis of biocompatible gold nanoparticles using dextrin as capping agent. Journal of Nanoparticle Research, 13(7), 2843-2851. DOI 10.1007/s11051-010-0172-3.
7. Zhang, D., Huang, M. C., and Alocilja, E. C. 2010. A Multiplex Nanoparticle-based Bio-barcoded DNA Sensor for the Simultaneous Detection of Multiple Pathogens. Biosensors and Bioelectronics, 26(4), 1736-1742.
8. Zhang, D., Carr, D. J., and Alocilja, E. C. 2009. Fluorescent bio-barcode DNA assay for the detection of *Salmonella enterica* serovar Enteritidis. Biosensors and Bioelectronics, 24(5), 1377-1381.

What is claimed is:

1. A method for making and testing an identifiable article of manufacture, the method comprising:
   (a) providing a first serialized oliqonucleotide-nanoparticle and a second serialized oliqonucleotide-nanoparticle, wherein:
      the first serialized oliqonucleotide-nanoparticle comprises (i) a first nanoparticle core and (ii) at least one first serialized oliqonucleotide attached thereto and having a first oliqonucleotide base sequence corresponding to a unique preselected code defining one or more identifying indicia of an article, and
      the second serialized oliqonucleotide-nanoparticle comprises (i) a second nanoparticle core and (ii) at least one second serialized oliqonucleotide attached thereto and having a second oliqonucleotide base sequence at least partially complementary to the first serialized oliqonucleotide and capable of hybridizing thereto;
   (b) affixing the first serialized oliqonucleotide-nanoparticle to an article, wherein the unique preselected code of the first oliqonucleotide base sequence defines the one or more identifying indicia of the article to which it is affixed;
   (c) releasing the article into a stream of commerce at a first point; and
   (d) recovering the article from the stream of commerce at a second point;
   (e) combining (i) at least one of the article and a sample thereof containing the first serialized oligonucleotide-nanoparticle and (ii) the second serialized oligonucleotide-nanoparticle under conditions sufficient for hybridization between the first serialized oligonucleotide and the second serialized oligonucleotide, thereby forming a nanoparticle complex comprising the first nanoparticle core attached to the second nanoparticle core via the hybridized first and second serialized oligonucleotides;
   (f) separating the nanoparticle complex from the article or the sample components remaining after nanoparticle complex formation, thereby forming a purified nanoparticle complex; and
   (g) electrochemically detecting the at least one of the first nanoparticle core and the second nanoparticle core in the purified nanoparticle complex, thereby determining at least one of the identifying indicia corresponding to the preselected code of the first serialized oligonucleotide.

2. The method of claim 1, wherein:
   (i) the first nanoparticle core comprises a metal, and the second nanoparticle core comprises a magnetic material; or
   (ii) the first nanoparticle core comprises a magnetic material, and the second nanoparticle core comprises a metal.

3. The method of claim 2, wherein:
   (i) the first nanoparticle core comprises the metal; and
   (ii) the second nanoparticle core comprises the magnetic material.

4. The method of claim 3, wherein the magnetic material is selected from the group consisting of magnetic iron oxides.

5. The method of claim 3, wherein the metal is selected from the group consisting of lead, cadmium, zinc, copper, tin, gold, silver, platinum, palladium, ruthenium, rhodium, osmium, and iridium.

6. The method of claim 2, wherein:
   (i) the first nanoparticle core comprises the magnetic material; and
   (ii) the second nanoparticle core comprises the metal.

7. The method of claim 6, wherein the magnetic material is selected from the group consisting of magnetic iron oxides.

8. The method of claim 6, wherein the metal is selected from the group consisting of lead, cadmium, zinc, copper, tin, gold, silver, platinum, palladium, ruthenium, rhodium, osmium, and iridium.

9. The method of claim 1, wherein the first nanoparticle core and the second nanoparticle core each independently have a size ranging from 1 nm to 1000 nm.

10. The method of claim 1, wherein the first serialized oligonucleotide and the second serialized oligonucleotide each independently have from 5 bases to 100 bases forming their respective oligonucleotide base sequences.

11. The method of claim 1, wherein the first serialized oligonucleotide and the second serialized oligonucleotide have the same coding lengths.

12. The method of claim 1, wherein the first serialized oligonucleotide and the second serialized oligonucleotide have different coding lengths.

13. The method of claim 1, wherein:
(i) the article comprises a plurality of first serialized oligonucleotide-nanoparticles affixed thereto;
(ii) each first nanoparticle core comprises a metal; and
(iii) the plurality of first serialized oligonucleotide-nanoparticles comprises a plurality of different metals in a preselected ratio corresponding to an additional preselected code defining one or more additional identifying indicia of the article.

14. The method of claim 1, further comprising performing at least one of PCR analysis and DNA sequencing analysis on the purified nanoparticle complex to determine all or a portion of the oligonucleotide base sequence of at least one of the first serialized oligonucleotide and the second serialized oligonucleotide.

15. The method of claim 1, wherein the article is selected from the group consisting of electronic/computer hardware, software encoded in a tangible medium, a pharmaceutical composition, a medical device, a legal instrument, a financial instrument, a food item, and packaging for a product.

16. The method of claim 1, wherein the first serialized oligonucleotide-nanoparticle is incorporated into the article in at least one medium selected from the group consisting of an ink applied to the article or a packaging material therefor, a label applied to the article or a packaging material therefor, and a resin or polymer medium as a component of or applied to the article or a packaging material therefor.

17. The method of claim 1, wherein the identifying indicia are selected from the group consisting of source information, supply chain information, product information, and combinations thereof.

18. The method of claim 17 wherein the identifying indicia are selected from the group consisting of a supplier identifier for the article, a production identifier for the article, a shipping identifier for the article, a product information identifier, and combinations thereof.

19. The method of claim 17 wherein the identifying indicia is a supplier identifier for the article selected from the group consisting of supplier name, supplier address, and combinations thereof.

20. The method of claim 17 wherein the identifying indicia is a production identifier for the article selected from the group consisting of production facility, production date, and combinations thereof.

21. The method of claim 17 wherein the identifying indicia is a shipping identifier for the article selected from the group consisting of shipping facility, shipping date, and combinations thereof.

22. The method of claim 17 wherein the identifying indicia is a product information identifier for the article selected from the group consisting of product code, product lot, product serial number, and combinations thereof.

23. The method of claim 2, wherein:
the metal is selected from the group consisting of lead, cadmium, zinc, copper, tin, gold, silver, platinum, palladium, ruthenium, rhodium, osmium, and iridium; and
the magnetic material is selected from the group consisting of magnetic iron oxides.

24. The method of claim 23, wherein part (g) comprises electrochemically detecting the metal to determine at least one of the identifying indicia corresponding to the preselected code of the first serialized oligonucleotide.

25. The method of claim 24, wherein part (g) further comprises performing acidic dissolution of the metal in the nanoparticle complex to form metal ions corresponding to the metal.

26. The method of claim 24, wherein part (f) comprises magnetically separating the nanoparticle complex from the article or the sample components remaining after nanoparticle complex formation via the magnetic material.

* * * * *

SEQUENCE LISTING

<160> NUMBER OF SEQ ID NOS: 2

<210> SEQ ID NO 1
<211> LENGTH: 26
<212> TYPE: DNA
<213> ORGANISM: Artificial Sequence
<220> FEATURE:
<223> OTHER INFORMATION: Synthetic oligonucleotide

<400> SEQUENCE: 1
aatatgctgc ctactgccct acgctt        26

<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 2
agatttaaat ctggtagaaa ggcgg        25